United States Patent [19]

Vinson et al.

[11] Patent Number: 4,691,558
[45] Date of Patent: Sep. 8, 1987

[54] PRESSURE PULSE GELATION TEST APPARATUS AND METHOD

[75] Inventors: Edward F. Vinson, Duncan; William H. Smith, Walters, both of Okla.

[73] Assignee: Halliburton Company, Duncan, Okla.

[21] Appl. No.: 876,969

[22] Filed: Jun. 19, 1986

[51] Int. Cl.⁴ ............................................ G01N 11/00
[52] U.S. Cl. ...................................................... 73/64.1
[58] Field of Search ................................... 73/64.1, 55

[56] References Cited

U.S. PATENT DOCUMENTS

| | | | |
|---|---|---|---|
| Re. 30,767 | 10/1981 | Felber et al. | 166/261 |
| 2,435,416 | 2/1948 | Thomson et al. | |
| 2,952,152 | 9/1960 | Fisher et al. | |
| 3,587,295 | 6/1971 | Simons | 73/64.1 |
| 3,900,290 | 8/1975 | Hornstra | 73/64.1 X |
| 4,109,159 | 8/1978 | Onillon et al. | 250/564 |
| 4,274,283 | 6/1981 | Maus et al. | 73/153 |
| 4,299,118 | 11/1981 | Gau et al. | 73/59 |
| 4,341,111 | 7/1982 | Husar | 73/64.1 |
| 4,484,468 | 11/1984 | Gau et al. | 73/60 |
| 4,484,821 | 11/1984 | Willcock | 374/24 |
| 4,599,891 | 7/1986 | Brauer et al. | 73/38 |

OTHER PUBLICATIONS

SPE 9285, "Transition Time of Cement Slurries Between the Fluid and Set State".
Page 3897 of vol. 41 of the Halliburton Services Sales & Service Catalog.

Primary Examiner—Michael J. Tokar
Assistant Examiner—Joseph W. Roskos
Attorney, Agent, or Firm—Joseph A. Walkowski; E. Harrison Gilbert, III

[57] ABSTRACT

The gelation testing apparatus includes a closed fluid circuit in which a sample of the substance to be tested is contained. A pressurizing device, such as a pump, is connected into the closed fluid circuit so that the pressure within the closed circuit can be changed. A pressure detecting device, such as a differential pressure transducer, is connected into the closed fluid circuit for detecting a pressure differential across the sample in response to the operation of the pressurizing device. Through the pressurizing device, the system pressure can be subjected to oscillating pressure pulses. The apparatus also can have the ability to control the temperature of the sample. This apparatus is used by placing the sample in the closed fluid circuit, creating a pressure pulse within the closed fluid circuit on one side of the sample, and detecting whether the pressure pulse is transmitted across the sample. This can be performed under controlled pressure and temperature conditions.

25 Claims, 5 Drawing Figures

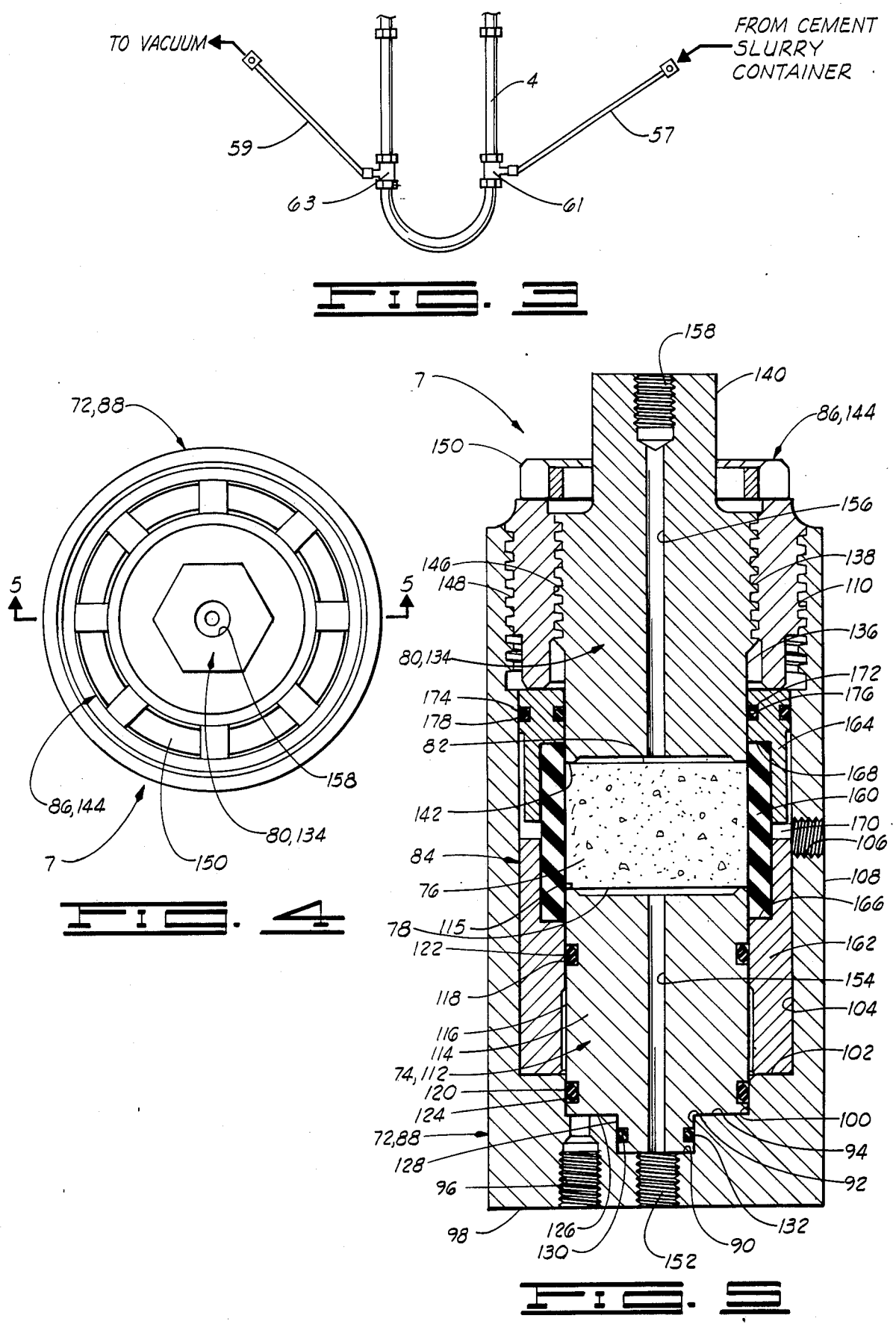

PRESSURE PULSE GELATION TEST APPARATUS AND METHOD

BACKGROUND OF THE INVENTION

This invention relates generally to apparatus and methods for testing gelation of a substance and more particularly, but not by way of limitation, to pressure and temperature controlled pressure pulse gelation test apparatus and methods.

The drilling and completing of oil or gas wells requires the use of various types of blended substances, some of which need to cure, gel or polymerize over time to be properly useful once they are placed in the well (the term "gel" and its formatives will be used herein as the generic term encompassing the phenomena for which the present invention is used). For example, sealants comprising silicate solutions are blended and flowed into a well for sealing water zones.

Because blended substances such as the exemplary sealant experience a transition in fluid characteristics in the gelling process and because such transition affects the ability of the substance to be pumped into the formation, it is important to know the gelling time characteristics of the compositions, in general, and of specific batches of a composition, in particular. It is also important to know the gel strength characteristic of a substance once it has gelled so that one will know which substance to use for a particular strength requirement. Such characteristics need to be determined with reference to selectable temperatures and pressures which correspond to those that will likely affect the substance in the actual environment in which it is to be used. Therefore, there is the general need for an apparatus and method for testing these gelation characteristics of a substance.

An accurate method for measuring the onset or initiation of gelation of a substance at selectable temperatures and pressures has been a problem because prior techniques have been too subjective or labor-intensive or they have degraded the tested substance when it is of a type having a weak initial gel structure. An example of the former shortcoming is found in columns 5 and 6 of U.S. Pat. No. Re. 30,767. Another example is that of the visual means of detection heretofore used. In this visual means, the solution or blend to be tested is prepared and placed in a glass bottle. By periodically tilting the bottle, one can easily observe if the sample is still fluid or if it has gelled. This technique is limited to lower temperature environments. For higher temperature tests, an oil bath with a water based test sample is placed in a glass pressure bottle. This method is unsafe for general usage because at a temperature of 250° F., for example, the pressure in the bottle could be sufficiently great (e.g., 30 psi) to create a high risk of injury from flying glass and from the reaction between the superheated water and oil if the pressure bottle ever exploded while it is being manually inspected.

Prior techniques which degrade a substance having a weak initial gel structure, and thus techniques which would yield inaccurate results as to such a substance, are devices referred to as viscometers or consistometers or thickening time/gel strength testers utilizing paddle/container combinations exhibiting relative movement between the paddle and container. Although the relative movement between these components can be very slow, it still exerts a sufficient mechanical action to degrade weak gel structures.

Therefore, there is the need for an improved apparatus and method for testing gelation, such as gel transition time and gel strength phenomena, in samples of substances having even relatively weak gel forming structures. Such an apparatus and method should be designed for making such tests under controllable temperature and pressure conditions, such as the high temperatures and pressure which will be encountered in a well. Such an improved apparatus and method should also be relatively easy and safe to use.

SUMMARY OF THE INVENTION

The present invention overcomes the above-noted and other shortcomings, and meets the aforementioned needs, by providing a novel and improved apparatus and method for testing gelation of a sample. In its preferred embodiment, the present invention provides an apparatus and method for measuring the initiation of gelation and for measuring gel strength. These measurements can be performed under controllable temperature and pressure conditions. The apparatus and method of the present invention are relatively easy and safe to use.

The apparatus of the present invention includes fluid circuit means, having a closable internal volume, for receiving the sample within the internal volume; pressurizing means, connected into the fluid circuit means, for changing the pressure within the internal volume; and pressure detecting means, connected into the fluid circuit means for detecting a pressure differential across the sample in the internal volume in response to the pressurizing means when the internal volume is closed. This apparatus further comprises means for changing the temperature of the sample in the internal volume. In the preferred embodiment, the pressurizing means includes means for creating pressure pulses within the internal volume on one side of the sample.

The method of the present invention comprises placing the sample in a closed fluid circuit, creating a pressure pulse within the closed fluid circuit on one side of the sample, and detecting whether the pressure pulse is transmitted across the sample. For determining a gelation time of the sample, this method includes repeating the steps of creating a pressure pulse and of detecting whether the pressure pulse is transmitted across the sample and also includes monitoring changes in the results of the repeated steps of detecting whether the pressure pulse is transmitted across the sample. To determine the gel strength of the sample, the method also includes repeating the steps of creating a pressure pulse and of detecting whether the pressure pulse is transmitted across the sample, and monitoring changes in the results of the repeated steps of detecting whether the pressure pulse is transmitted across the sample. This method can also be performed by applying a selectable pressure to the sample in the closed fluid circuit. It can also be performed by taking the sample in the closed fluid circuit to a selectable temperature.

Therefore, from the foregoing, it is a general object of the present invention to provide a novel and improved apparatus and method for testing gelation of a sample. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 3 shows a modification to the spcific implementation of FIG. 2 for particular use in testing a cement slurry.

FIG. 4 is a top view of a preferred embodiment of a core sample holder forming part of a preferred embodiment of the present invention useful for testing a gel forming treatment fluid.

FIG. 5 is a sectional view of the core sample holder as taken along line 5—5 in FIG. 4.

DETAILED DESCRIPTION OF THE PREFERRED EMBODIMENTS

Figure 1:
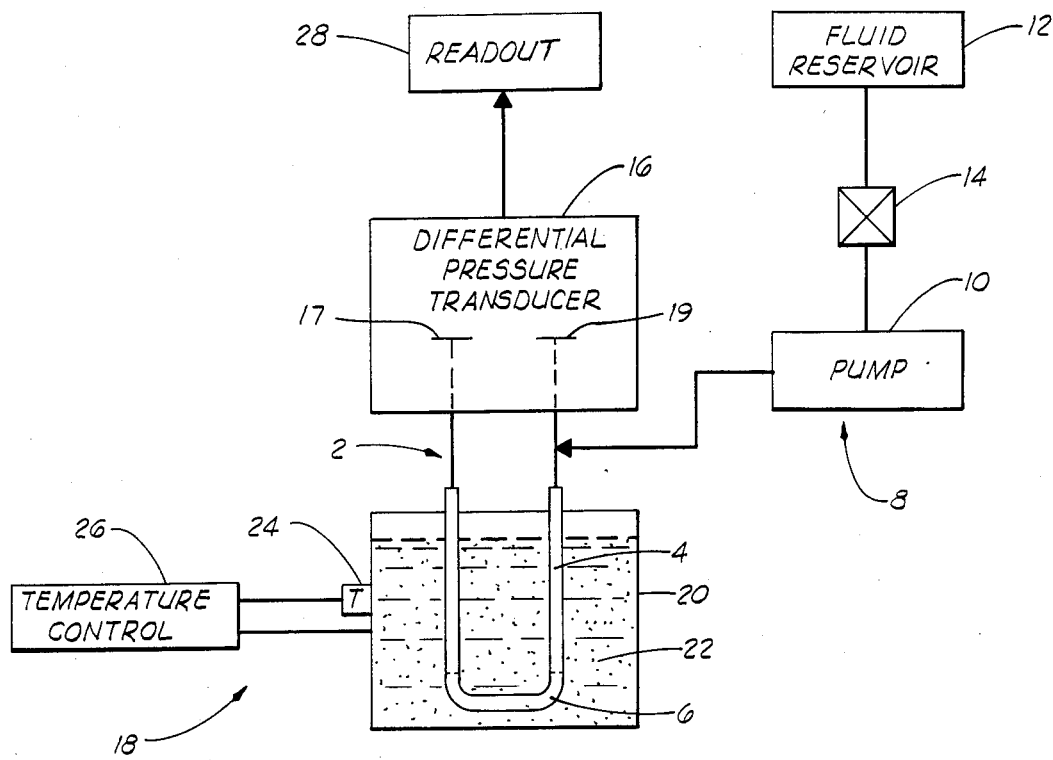
FIG. 1 is a block diagram of a preferred embodiment of the apparatus of the present invention.

A preferred embodiment of the apparatus of the present invention is schematically illustrated in FIG. 1. The construction of this embodiment lends itself to usage both in a laboratory and in the field. The present invention also lends itself to usage not only in the oil and gas industry, but also in other industries where gelation testing is needed. An example of such other industry might be the food industry. This embodiment is used to test gelation of a sample of any suitable substance. Examples of such a suitable substance include hydratable polysaccharides, comprising galactomannan or glucomannan gums, such as guar gum, derivatized guars such as hydroxypropyl guar and carboxymethyl hydroxypropyl guar. Also suitable are celluluose derivatives, such as hydroxyethyl cellulose, carboxymethyl cellulose, and carboxymethylhydroxyethyl cellulose as well as hydratable synthetic polymers and copolymers such as polyacrylate, polymethacrylate and polyacrylamide. The foregoing hydratable polysaccharides and synthetic polymers can be crosslinked with any suitable crosslinking agents well known in the art, including various titanium chelates, zirconium chelates, potassium pyroantimonates, zirconium oxychloride as well as various aluminum compounds such as aluminum acetate and the like. In a similar fashion gelling agents for cement and cement including such gelling agents might be tested. Such cement agents are commonly known as fluid loss additives and include cellulose derivatives such as hydroxyethyl cellulose and various crosslinkers used with the same. It should also be noted that various cement retarders and accelerators also affect the gelation properties of cement, and that therefore the present invention is highly useful in ascertaining the effects of these products on the cement. These examples, however, are not to be taken as limiting either specific or general types of substances that can be tested in the present invention.

The apparatus depicted in FIG. 1 includes fluid circuit means 2, having a closable internal volume, for receiving the sample within the internal volume. The circuit means 2 includes a U-shaped tube 4 having a sample 6 disposed in the bottom receptacle portion (as viewed in FIG. 1) of the tube 4 interconnecting the two legs thereof. Although the circuit means 2 is illustrated in FIG. 1 as a U-shaped tube, it is contemplated that any suitable closed container with a pulse entry and exit means can be used. By way of example, other possible containers include a straight tube, a coil, a closed chamber such as in a core sample holder, or a sand-packed tube. A particular embodiment of a core sample holder is illustrated in FIGS. 4 and 5. This holder, generally identified by the reference numeral 7, will be more particularly described hereinbelow. Defining the fluid circuit means 2 as having a "closable internal volume" or as being a "closed" circuit does not imply that the volume or circuit is necessarily closed on itself whereby fluid flow would be continuous from and back to a starting point; rather it simply means closed as to pressure and as to pressure effects imposed upon the sample.

The embodiment shown in FIG. 1 also includes pressurizing means 8, connected into the fluid circuit means 2, for changing the pressure within the internal volume. The pressurizing means 8 of this illustrated embodiment includes a pump 10 which is shown connected for pumping a suitable fluid into the fluid circuit means 2 from a fluid reservoir 12 connected to the pump 10 through an isolation valve 14. Although this is one means for establishing a selectable pressure in the fluid circuit means 2, a preferred means includes components independent of the pump 10 as will be further explained hereinbelow with reference to the specific implementation of FIG. 2. Whether used to bring the internal volume to a selectable working pressure, the pump 10 does provide means for creating pressure pulses within the internal volume on one side of the sample 6.

The embodiment shown in FIG. 1 still further includes pressure detecting means 16, shown specifically as a differential pressure transducer connected into the fluid circuit means 2, for detecting a pressure differential across the sample 6 in the internal volume in response to the pressurizing means 8 when the internal volume is closed, as depicted by the two closed ends 17, 19.

The FIG. 1 embodiment further comprises means 18 for changing the temperature of the sample 6 in the internal volume. The means 18 can be implemented by any suitable means. Examples include a sand bath, a water bath or heat tape; however, other suitable means, whether operating in response to electricity, combustion or other chemical reaction or otherwise, can be used. For purposes of illustration, the means 18 depicted in FIG. 1 includes a receptable 20 containing a bath 22 in which the tube 4 is disposed. A temperature probe 24 and a temperature controller 26 are used to control the temperature of the bath 22, which in turn controls the temperature of the sample 6 through heat conduction through the wall of the tube 4.

The embodiment shown in FIG. 1 also includes monitor means for monitoring the output of the pressure detecting means 16. This monitor means can be any suitable device by which a reading of the detected pressure is provided. Contemplated examples include a voltmeter, a computer (which would be useful in rejecting small signals to a certain threshold), or a recorder. In FIG. 1 the monitor means is shown embodied as a readout device 28 containing known circuits such as a visual numeric display and conditioning circuitry by which the signals from the pressure detecting means are utilized or converted into signals for actuating the visual numeric display to display a detected pressure differential.

Figure 2:
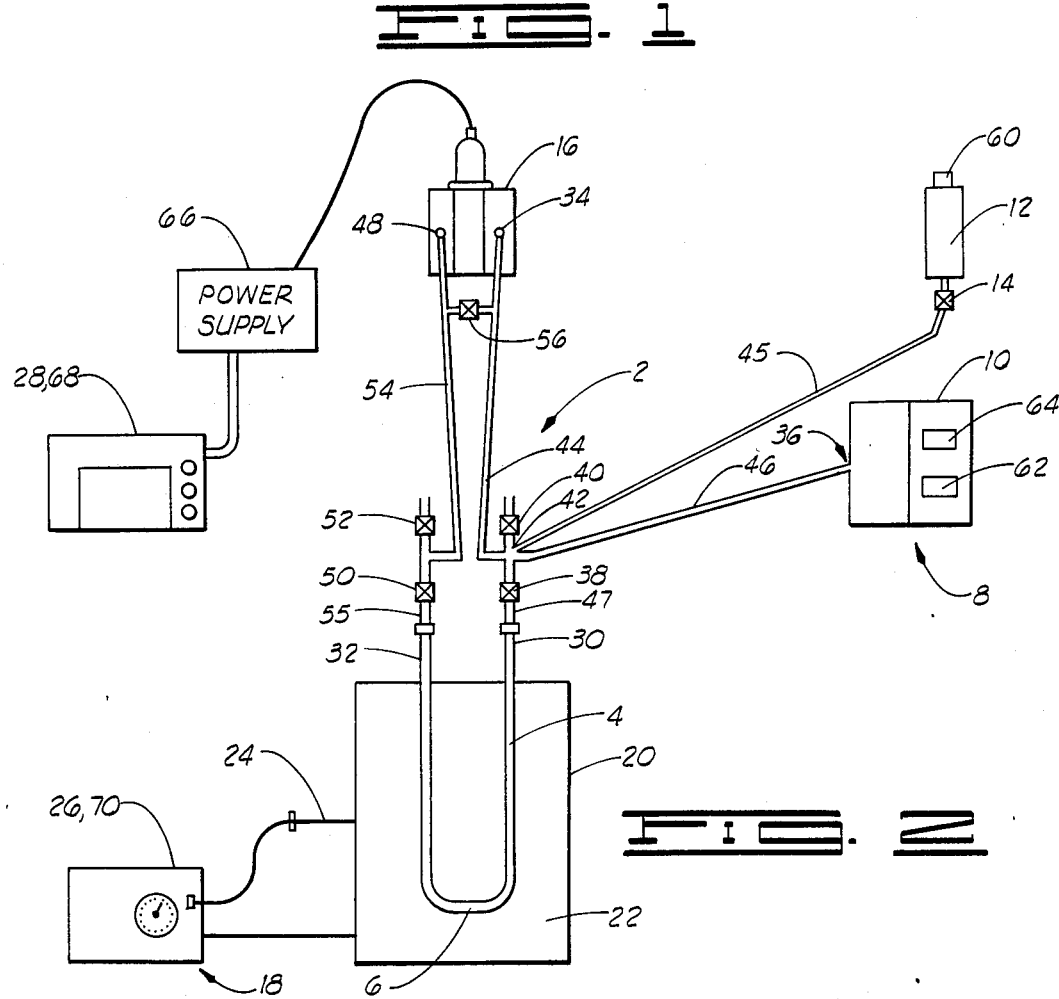
FIG. 2 is a schematic diagram of a specific implementation of another preferred embodiment similar to the one illustrated in FIG. 1.

A specific implementation of the embodiment shown in FIG. 1 (except for a change in the pressurizing means 8) is schematially illustrated in FIG. 2. Portions of the specific implementation shown in FIG. 2 corresponding to portions identified in FIG. 1 are indicated by like reference numerals.

The fluid circuit means 2 of this embodiment includes the U-shaped tube 4 which has two ends 30, 32 protruding out of the receptable 20 and the bath 22. The U-tube 4 is a hollow tubing, the hollow interior of which defines at least part of the internal volume of the fluid circuit means 2 in which the sample 6 is received. The tubing is made of any suitable substance, such as stainless steel or Monel metal.

The fluid circuit means 2 also includes means for connecting the end 30 of the U-tube 4 to a port 34 of the differential pressure transducer 16, to an outlet 36 of the pump 10, and to the valve 14 through which a pressurized fluid is provided to the fluid circuit withou first passing through the pump 10. This means includes an insolation valve 38 and a valve 40 which are connected in common at a fluid conducting joint 42. The joint 42 also connects to the port 34 through a tubing or pipe 44 made of a suitable substance, such as Monel metal. The joint 42 is also connected to the outlet 36 of the pump 10 through a tubing or pipe 46 made of a suitable substance, which is stainless steel in the disclosed embodiment. A similar suitable tubing 45 connects the valve 14 to the joint 42. The valve 38 is connected to the end 30 by a coupling 47, and the valve 40 provides a means for loading or unloading samples and removing unwanted air from the system.

The fluid circuit means 2 of the FIG. 2 implementation includes means for connecting the end 32 of the U-tube 4 to a port 48 of the differential pressure transducer 16. This means includes an isolation valve 50, a valve 52 and a tubing or pipe 54 interconnecting the valves 50, 52 with the port 48. The tubing or pipe 54 is made of a suitable substance, such as Monel metal in the illustrated embodiment. The valve 50 is connected to the end 32 by a coupling 55, and the valve 52 provides a means for loading or unloading samples and removing unwanted air from the system.

An alternative to using the valves 40, 52 for loading and unloading the samples into and from the internal volume of the fluid circuit means 2 is illustrated in FIG. 3, which shows the tube 4 modified to connect with a conduit 57 and a conduit 59. The conduit 57 directly couples or communicates a source of the sample into the receptacle portion of the tube 4 where the sample is to be maintained for testing. This allows the sample, such as the cement slurry indicated in FIG. 3, to flow into the receptacle without passing through any of the aforementioned valves of the system. This precludes abrading or fouling of the valves with particularly deleterious substances such as the exemplary cement slurry. The conduit 59 allows the sample to be directly removed from the fluid conduit without passing through the valves of the system. For example, the conduit 59 can be connected to or communicated with a vacuum (as labeled in FIG. 3) which extracts or removes the exemplary cement slurry from the ssytem after the testing has been performed in the sample but before the slurry can sufficiently set up to the point where it cannot be removed from the tube 4 without destroying the tube. This allows the tube 4 to be reused to test other samples. The conduits 57, 59 are suitable tubing connected to the tube 4 by couplings 61, 63, respectively.

Referring to the FIG. 2 implementation, interconnecting the tubings or pipes 44, 54 is an equalization valve 56, forming another part of the fluid circuit means 2 of the implementation illustrated in FIG. 2.

The pressurizing means 8 of the FIG. 2 implementation includes the pump 10 having the outlet 36. The pump 10 is of any suitable type which can be actuated so that its operation creates one or more pressure pulses in the fluid upon which it acts through the outlet 36 and the tubing 46. Thus, a fixed stroke pump can be used; however, a variable stroke pump is contemplated to be preferable because the pulse magnitude can be increased by lengthening the stroke even if pressure has to be reduced within the fluid circuit means (such as to prevent gasket failure at high temperatures).

In a specific implementation the pump 10 is one from which an outlet check valve has been removed. With the check valve removed, the pump 10 provides means for creating pressure pulses within the internal volume on one side of the sample 6, the purpose for which will be more particularly described hereinbelow. If the check valve were retained, the pump 10 could function as illustrated in FIG. 1 to provide means for pumping a fluid into the internal volume of the fluid circuit means 2 for applying a selectable pressure to the sample 6.

To control the pump 10, there is included a pump rate adjustment control mechanism 62 and a system pressure readout device 64 of types known to the art for controlling and monitoring the operation of the pump 10. Although not shown, the pump 10 preferably also includes an automatic shut-off control mechanism of a type as known to the art for disabling the pump 10 if an excessive pressure is detected.

Although the illustrated embodiments show a pump 10 to effect the pulse generation means, it is contemplated that other suitable pulse creating means can be used within the present invention. Examples of such other means are a solenoid acting on a plunger, a hydraulically driven plunger, a pneumatically driven plunger, and a diaphragm driven by pneumatics, hydraulics or a cam to displace it.

The pressurizing means of the FIG. 2 embodiment includes the reservoir 12 and the valve 14 functioning independently of the pump 10 to bring the system to a selectable working pressure. A suitable fluid moving device 60, such as a hand pump or a pressurized gas (e.g., nitrogen), moves an inert fluid for that environment (e.g., water if the sample is cement) from the reservoir 12 through the isolation valve 14 and into the fluid circuit means 2 through the conduit 45 and the open isolation valves 38, 50 and the open equalization valve 56. This places the inert fluid on both sides of the sample 6 in the tube 4.

The differential pressure transducer 16 has the aforementioned two ports 34, 48. In the illustrated embodiment of FIG. 2, the port 34 is referred to as the high pressure side port, and the port 48 is referred to as the low pressure side port. This is because the oscillating pressure pulses exerted by the pump 10 are created on the port 34 side of the transducer 16. Although not illustrated, the preferred embodiment transducer 16 is of a type which has a respective bleed valve associated with each of its ports. This preferred embodiment type can also be of a type which has a very high sensitivity so that relatively small pressure differentials will be detected across a sample which has a very weak gel structure.

The particular embodiment of the transducer 16 shown in FIG. 2 is illustrated as being energized by a power supply 66 of a suitable type. For example, the power supply 66 can be a 110 VAC power source, a truck battery, a portable generator, or other suitable energy supply. FIG. 2 further shows that the output from the transducer 16, which in the preferred embodiment comprises electrical signals representing differential pressures detected between the ports 34, 48, is provided through the power supply 66 to a chart recorder 68 defining the illustrated specific embodiment of the readout means 28. These electrical signals from the transducer 16, and the resultant visual graphical output of the chart recorder 68, represent a measure of the transmissability of the pressure pulses across or through the sample, which transmissability corresponds to the gelation of the sample. In particular, this correspondence is in inverse proportion in that the more gelled the sample becomes, the less the pressure pulses are transmitted whereby the graphical respresentation generated by the chart recorder 68 trends from showing substantially no pressure differential when the sample is completely fluid to showing substantially the full pressure pulse pressure differential when the sample is fully gelled.

The specific implementation illustrated in FIG. 2 also includes the temperature changing means which comprises the receptacle 20, the bath 22 (a fluidized sand bath in the specific implementation), the temperature probe 24 and the temperature controller 26. The temperature controller 26 is specifically implemented by a thermoregulator 70. The temperature probe 24 and the thermoregulator 70 define a means for controlling the temperature of the bath 22 in a manner as known to the art.

The aforementioned components of the preferred embodiment and its specific implementation shown in FIGS. 1 and 2 are of suitable, conventional types known to the art; therefore, these components will not be further described.

To utilize the apparatus shown in FIGS. 1 and 2, the closed fluid circuit is opened to allow the sample 6 to be placed in the bottom of the U-tube 4. This can be accomplished by, for example, disconnecting one of the couplings 47, 55 and flowing the sample into the tube 4 through the respective opened end or, alternatively, by injecting the sample through the valve 40 or 52. The system is then closed, such as by reconnecting the respective coupling or closing the respective valve, but with the differential pressure transducer 16 and the pump 10 connected in communication with the fluid circuit 2 as illustrated in FIGS. 1 and 2. That is, the ports 34, 48 of the differential pressure transducer 16 are connected across the ends 30, 32 of the U-tube 4, and the outlet 36 of the pump 10 is connected in communication with one side of the differential pressure transducer and the corresponding end of the tube thereby defining that side as the high pressure side (the port 34/end 30 side in the illustrated embodiment).

The bleed valves of the differential pressure transducer are closed, and the isolation valves 14, 38, 50 and the equalization valve 56 are opened. The system is then taken to any desired pressure by, for the FIG. 2 implementation, flowing the inert fluid from the reservoir 12 through these open valves under pressurizing force of the pressurized nitrogen in the device 60. This flow into the system continues until a selectable pressure is exerted on the sample 6. When this pressure is reached, the valve 14 is closed to shut off further flow of the nitrogen. The sample is also taken to the desired test temperature by being heated through operation of the thermoregulator 70 and the resultant heat transfer from the fluidized sand bath 22 to the sample 6 across the wall of the U-tube 4.

Once the system has been taken to the desired pressure and temperature, the equalization valve 56 is closed. The pump 10 is then operated to create a pressure pulse in the fluid contained within the closed fluid circuit 2 with each stroke of the pump, thereby creating oscillating pulses with a plurality of pump strokes. The oscillating pressure pulses are applied to the high pressure side between the port 34 of the differential pressure transducer 16 and the end of the sample 6 nearer the end 30 of the tube 4. The creation of pressure pulses can occur after, or concurrently with, pressure and temperature modifications.

The output of the differential pressure transducer 16 is monitored to detect pressure differentials across the sample 6 in response to the oscillating pressure pulses created by the pump 10. This monitoring is done in the FIG. 2 embodiment by operating the chart recorder 68 and observing the graphical output. This graphical output will show, for the preferred embodiment, that no, or substantially no, pressure differentials are detected as long as the test sample 6 remains fluid because the pulses are transmitted through or across the fluid sample. When the sample gels sufficiently, however, the gelled sample isolates the low pressure side port 48 from the pressure pulse applied to the port 34 side of the sample 6. This isolation creates a pressure differential which is repeated in correspondence to the created oscillating pressure pulses. These pressure differentials are detected by the transducer 16 and displayed on the chart recorder 68.

From the foregoing it is apparent that the method of the described embodiments broadly comprises placing the sample 6 in the closed fluid circuit 2, creating a pressure pulse within the closed fluid circuit 2 on one side of the sample 6, and detecting whether the pressure pulse is transmitted across the sample 6. In the described embodiments, this method further comprises applying a selectable pressure, such as one different from atmospheric pressure, to the sample 6 in the closed fluid circuit 2. Another step included in the illustrated embodiments is that of taking the sample 6 in the closed fluid circuit 2 to a selectable temperature. This step can be performed before or concurrently with the step of creating a pressure pulse. This method also includes the steps of determining a gelation time of the sample and of determining the gel strength of the sample.

The step of determining a gelation time of the sample includes repeating the steps of creating a pressure pulse and of detecting whether the pressure pulse is transmitted across the sample. It also includes the step of monitoring changes in the results of the repeated steps of detecting whether the pressure pulse is transmitted across the sample. That is, as previously described, a plurality of pressure pulses are generated in an oscillating manner so that the transmissability, and thus the gelation, of the sample 6 can be determined by detecting the responsiveness of the pressure transducer 16 to the oscillating pressure pulses. For the extremes of no gelation and full gelation, the monitored output of the pressure transducer 16 will reflect substantially no pressure differential and substantially full pressure differential, respectively.

The step of determining the gel strength of the sample includes the same steps as those of the step of determining the gel time. That is, multiple pressure pulses are applied by the pump 10 and the resulting pressure differentials across the sample 6 are monitored. In a particular methodology of incrementally testing the gel strength, determining the gel strength includes the additional step of increasing the pressure magnitude of the pressure pulse for successive ones of the repeated steps of creating a pressure pulse; however, this is not in general required because suitably large, constant magnitude pulses can be repetitively applied to test for gel strength. By applying suitably sized pressure pulses, the responsiveness of the sample 6 to the pressure pulses creates outputs through the differential pressure transducer 16 indicative of the gel strength of the sample 6. For example, pressure pulses of up to 250 pounds per square inch, or greater, might be generated and applied to the sample 6.

Once pressure differentials have been obtained, they can be used with the known specific test volume dimensions, such as the length and diameter of the pertinent volume of the tube 4 in the FIG. 2 embodiment, to determine information about the sample. For example, by using these values in known calculations of types used in cementing practice, a static gel strength of a tested cement sample can be determined.

The above-described method can be implemented with the embodiments shown in FIGS. 1 and 2. It is contemplated that the method of the present invention can be implemented with other apparatus. To this end, another embodiment of a fluid circuit 2, or at least a part of one, is illustrated in FIGS. 4 and 5. This is the core sample holder 7 referred to hereinabove. The holder 7 can be coupled in place of the U-tube 4 with components similar or analogous to those shown in the FIG. 2 implementation as would be readily apparent to those skilled in the art.

The core sample holder 7 is used to test a core sample taken from a well to be treated such as for water or sand control purposes. Such a core sample is removed from the well by means well known in the art, which means are commonly known as "core guns." Once removed, the sample is impregnated with the gel forming treatment fluid with which the well is to be treated. This impregnation can occur either before or after the core sample is placed in the holder 7.

Once inside the holder and impregnated, the sample is subjected to pressurization and pulsing in manners similar or analogous to those described hereinabove. During pulsing, pressure differentials are detected across the impregnated core sample for making the gelation analyses described hereinabove. During this testing, the sample can also be heated within the holder 7 in any suitable manner as known to the art.

The use of a core sample also creates the possiblity of squeezing the sample to simulate pressure on the formation in which the tested fluid is to be used. Additionally, the impregnated core sample allows other testing to be performed on the gel with which the core sample is impregnated. For example, one can try to extrude the gel from the core sample after the gel has set, thereby giving additional useful information as to the characteristics of the gel in a real formation.

The embodiment of the holder 7 shown in FIGS. 4 and 5 includes a housing 72 in which a movable support means 74 for supporting a core sample 76 along a surface 78 thereof is movably disposed. Disposed in fixed relationship to the housing 72 is a fixed support means 80 for supporting the core sample 76 along a surface 82. The fixed support means 80 is spaced from the movable support means 74 so that a core sample receiving region is defined therebetween. This receiving region is located in FIG. 5 where the core sample 76 is shown. The holder 7 further includes means for communicating pressure to and from this core sample receiving region. Forming other parts of the holder 7 illustrated in FIGS. 4 and 5 are a gasket subassembly 84 and a closure means 86 for fixing the fixed support means 80 relative to the housing 72.

The housing 72 is defined by a cylindrical body 88 through which an axial chamber extends. The axial chamber is defined by an annular surface 90 defining the lowermost surface of the chamber within the body 88 as viewed in FIG. 5. Extending longitudinally from the outer perimeter of the annular surface 90 is a cylindrical surface 92 defining a piston sealing throat. Extending radially from the upper perimeter of the cylindrical surface 92 is an annular surface 94 defining a piston stop shoulder. Intersecting the surface 94 and extending therefrom is a port 96. The port 96 extends to a bottom surface 98 of the body 88. The port 96 provides a communication path through which pressure can be applied to a lower surface of the movable support means 74 for effecting squeezing of the core sample 76 as more particularly described hereinbelow.

Extending longitudinally from the surface 94 is a cylindrical surface 100 defining another sealing surface of the axial chamber of the body 88. Extending radially from the upper perimeter of the surface 100 is an annular surface 102 defining a support surface for a lower backup sleeve of the gasket subassembly 84 more particularly described hereinbelow. Extending longitudinally from the surface 102 is a cyindrical surface 104 defining a surface of a gasket cavity in which the gasket subassembly 84 is located. A radial port 106 is defined between the surface 104 and a cylindrical exterior surface 108 of the body 88. This port provides an inlet through which pressure or heat can be communicated to the gasket subassembly 84 such as for pressure balancing or for applying to the core sample 76.

Completing the definition of the axial chamber is a threaded cylindrical surface 110 extending longitudinally from the surface 104 and defining a coupling surface with which the closure means 86 engages.

Disposed in the lower portion of this axial chamber is the movable support means 74 which in the embodiment shown in FIG. 5 is defined by a piston 112 having a cylindrical main body 114 with a top annular surface 115 intersecting an outer surface 116 in which grooves 118, 120 are defined for receiving seal members such as O-rings 122, 124, respectively. Extending radially inwardly from the outer surface 116 opposite the surface 115 is an annular surface 126 terminating at the top perimeter of a cylindrical surface 128 defining a neck of the piston 112. A groove 130 carrying a seal member, such as an O-ring 132, is defined circumferentially around the surface 128. The seal member 132 engages the surface 92 of the housing body 88; the seal member 124 engages the surface 100 of the housing body 88; and the seal member 122 engages a surface of the gasket subassembly 84. The sizing of the piston 112 is such that is slidably received within the axial chamber of the housing body 88. The downward movement of the sliding relationship is limited when the surface 126 of the piston 112 engages the piston stop shoulder surface 94 of the housing body 88.

Disposed in the opposite end of the axial chamber from the piston 112 is the fixed support means 80 defined in the embodiment illustrated in FIG. 5 by a top plug 134 having a cylindrical main body with an outer surface 136 having a threaded portion 138. Radially inwardly offset from the surface 136 is a hexagonal surface 140 defining a neck of the top plug 134, which neck extends axially beyond the end of the housing 72. The plug 134 has a bottom surface 142 abutting the surface 82 of the core sample 76. This supports this end of the core sample 76 relative to the housing 72 because the plug 134 is fixed relative to the housing 72 by the closure means 86.

The means 86 is defined by a cylindrical nut 144 having an inner threaded surface 146 and an outer threaded surface 148. The nut is utilized by engaging lugs 150 shown in both FIGS. 4 and 5. When the nut 144 is attached to the housing 72, the threaded surface 146 engages the threaded portion 138 of the plug 134, and the outer threaded surface 148 engages the threaded surface 110 of the housing body 88.

With the core sample 76 retained between the piston 112 and the plug 134, pressure is communicated into the core sample receiving region of the axial chamber of the housing body 88 through the means for communicating referred to hereinabove. This means is defined in the FIG. 5 embodiment by a lower threaded bore 152 defining a pulse inlet/outlet aperture, by axial channels 154, 156, and by an upper threaded bore 158 defining a pulse inlet/outlet aperture. The threaded bore 152 extends axially between the bottom surface 98 an the annular surface 90 of the housing body 88. As illustrated, this bore is threaded to receive a suitable coupling of a conduit through which a pressurized fluid can be flowed. The channel 154 is defined axially through the piston 112 in communication with the bore 152. The axial channel 156 is similarly defined through the central length of the top plug 134 and extends into communication with the bore 158 defined at the top of the plug 134 as shown in FIG. 5. The bore 158 is also threaded to couple with a suitable conduit or other means by which a pressurized fluid can be communicated with the core sample holder 7.

To seal the core sample receiving region relative to the pressure which can be communicated thereto through the bores 152, 158 and the channels 154, 156, the FIG. 5 embodiment includes the gasket subassembly 84. This subassembly includes a sealing gasket 160 of a suitable material known to the art. The gasket 160 is supported in the gasket cavity of the cylindrical body 88 by a lower backup sleeve 162 and by an upper backup sleeve 164. The sleeve 162 has an annular surface 166 engaging a lower end surface of the gasket 160, and the sleeve 164 has an annular surface 168 engaging an upper end surface of the gasket 160. The sleeves 162, 164 extend towards each other but are spaced at their nearest edges so that an opening 170 is defined therebetween in communication with the radial port 106. The upper backup sleeve 164 has an inner circumferential groove 172 and an outer circumferential groove 174 in which sealing members 176, 178 are respectively received. The seal 176 seals between the upper sleeve 164 and the surface 136 of the plug 134, and the seal 178 seals between the upper sleeve 164 and the surface 104 of the gasket cavity defined within the housing body 88.

The gasket subassembly 84 prevents migration around the core sample 76. It is known, however, that the gasket 160 may extrude at higher temperatures if high pressures are maintained. The present invention can prevent this by allowing a lower pressure to be used with high temperatures while maintaining the ability to provide a suitably large pressure pulse. This is accomplished by utilizing in such a particular situation a longer pump stroke as would be available if the pump 10 is embodied by a variable stroke pump. By way of a particular example, if the core sample 76 were heated to 300° F. or 400° F., it might be necessary, depending upon the particular gasket material, to lower the pressure communicated through the bores 152, 158 and the channels 154, 156 from, for example, 1000 psi to 100 psi to prevent extrusion of the gasket. With a variable stroke pump, the stroke could be lengthened to yield an acceptably large pulse that would not otherwise be achievable if a fixed stroke pump were used. For example, with a fixed stroke pump giving a 250 psi pulse when the system pressure is at 1000 psi, only a 25 psi pulse would be provided by the same pump at the lower 100 psi reference pressure. This smaller pulse would be more difficult to detect and measure. Using a variable stroke pump instead of a fixed stroke pump would allow a pulse greater than 25 psi to be generated even at the 100 psi reference pressure.

For this embodiment shown in FIGS. 4 and 5, the previously described testing described with reference to FIG. 2 can be implemented for the fluid impregnating the core sample 76. In addition, a pressure can be applied through the port 96 to act on the annular surface 126 of the piston 112 to drive the piston 112 upwardly as viewed in FIG. 5. This causes the surface 115 of the piston 112 to engage the surface 78 of the core sample 76. Further upward movement of the piston 112 squeezes the core sample 76 to simulate a pressure acting on the formation from which the sample 76 was taken. Thus, the piston 112 is moved towards the stationary plug 134 to effect the squeezing of the core sample 76.

From the foregoing description it is apparent that the present invention includes no mechanical parts acting on the sample 6; therefore, the present invention is ideally suited for performing gelation tests on samples having weak gel structures because there is no mechanical agitation or substantial physical displacement of the sample. These gelation tests include, but are not necessarily limited to, onset of gelation, developing gel strength, and final gel strength. It is also contemplated that the present invention can be used for long-term aging tests. The present invention, however, is also suitable for use with other types of fluids. The present invention is also adaptable for both laboratory and field usage in various industries and such usage is relatively easy and safe.

Thus, the present invention is well adapted to carry out the objects and attain the ends and advantages mentioned above as well as those inherent therein. While preferred embodiments of the invention have been described for the purpose of this disclosure, numerous changes in the construction and arrangement of parts and the performance of steps can be made by those skilled in the art, which changes are encompassed within the spirit of this invention as defined by the appended claims.

What is claimed is:

1. An apparatus for testing gelation of a sample comprising:
   fluid circuit means, having a closeable internal volume, for receiving the sample within said internal volume;
   pressurizing means, including means for creating pressure pulses within said internal volume on one side of the sample, connected into said fluid circuit means, for changing the pressure within said internal volume; and pressure detecting means, connected into said fluid circuit means, for detecting a pressure differential across the sample in said internal volume in response to said pressurizing means when said internal volume is closed.

2. An apparatus as defined in claim 1, further comprising means for changing the temperature of the sample in said internal volume.

3. An apparatus as defined in claim 1, wherein:
said fluid circuit means includes a tube having two ends between which the sample is disposed when the sample is received in internal volume of said fluid circuit means;
said pressure detecting means includes a differential pressure transducer having a first port connected to one end of said tube and having a second port connected to the other end of said tube; and
said pressurizing means includes a pump having an outlet connected into said fluid circuit means in communication with said first port of said differential pressure transducer and said one end of said tube.

4. An apparatus as defined in claim 3, further comprising means for heating the sample when the sample is disposed in said tube.

5. An apparatus as defined in claim 3, further comprising readout means for displaying pressure differential signals output from said differential pressure transducer.

6. An apparatus as defined in claim 1, wherein:
said pressure detecting means includes a pressure transducer having a high pressure port and a low pressure port and having an output for providing electrical signals representing pressures detected between said high pressure port and said lower pressure port; and
said fluid circuit means includes:
a tube having a hollow interior, defining at least part of said internal volume, for receiving the sample;
means for connecting said lower pressure port of said pressure transducer to an end of said tube; and
means for connecting said high pressure port of said pressure transducer and said pressurizing means to another end of said tube.

7. An apparatus as defined in claim 6, further comprising means for heating the sample when the sample is disposed in said tube.

8. An apparatus as defined in claim 7, further comprising readout means, connected to said pressure transducer and responsive to said electrical signals, for displaying a detected pressure differential.

9. An apparatus as defined in claim 1, wherein said fluid circuit maans includes:
a housing;
movable support means, movably disposed in said housing, for supporting a core sample along a first surface thereof;
fixed support means, disposed in said housing in fixed relationship thereto, for supporting the core sample along a second surface thereof, said fixed support means spaced from said movable support means so that a core sample receiving region is defined therebetween; and means for communicating pressure to and from said core sample receiving region.

10. An apparatus for testing gelation of a sample, comprising:
fluid circuit means, having a closeable internal volume, for receiving the sample within said internal volume, said fluid circuit means including:
a receptacle connected to said pressurizing means and said pressure detecting means;
first conduit means for communicating a cement slurry directly into said receptacle; and
second conduit means for communicating the cement slurry directly out of said receptacle;
pressurizing means, connected into said fluid circuit means, for changing the pressure within said internal volume; and
pressure detecting means, connected into said fluid circuit means, for detecting a pressure differential across the sample in said internal volume in response to said pressurizing means when said internal volume is closed.

11. A method of testing gelation of a sample, comprising:
placing the sample in a closed fluid circuit;
creating a pressure pulse within the closed fluid circuit on one side of the sample; and
detecting whether the pressure pulse is transmitted across the sample.

12. A method as defined in claim 11, further comprising applying a selectable pressure to the sample in the closed fluid circuit.

13. A method as defined in claim 12, further comprising taking the sample in the closed fluid circuit to a selectable temperature.

14. A method as defined in claim 11, further comprising determining a gelation time of the sample, including:
repeating said steps of creating a pressure pulse and of detecting whether the pressure pulse is transmitted across the sample; and
monitoring changes in the results of the repeated steps of detecting whether the pressure pulse is transmitted across the sample.

15. A method as defined in claim 11, further comprising determining the gel strength of the sample, including:
repeating said steps of creating a pressure pulse and of detecting whether the pressure pulse is transmitted across the sample; and
monitoring changes in the results of the repeated steps of detecting whether the pressure pulse is transmitted across the sample.

16. A method as defined in claim 11, wherein detecting whether the pressure pulse is transmitted across the sample includes connecting a differential pressure transducer into the closed fluid circuit for detecting pressure differentials across the sample.

17. A method as defined in claim 16, wherein creating a pressure pulse includes:
connecting an outlet of a pump into the closed fluid circuit in fluid communication between the differential pressure transducer and one side of the sample; and
operating the pump with its check valve removed.

18. A method of testing gelation of a sample, comprising:
placing the sample in a tube;
connecting a differential pressure transducer to ends of the tube;

exerting with a fluid a selectable pressure on the sample in the tube;
creating pressure pulses in the fluid; and
monitoring an output of the differential pressure transducer to detect pressure differentials across the sample in response to the pressure pulses.

19. A method as defined in claim 18, further comprising controlling the temperature of the sample in the tube to a selectable temperature.

20. A method as defined in claim 19, wherein creating pressure pulses includes:
connecting a pump in communication with one side of the differential pressure transducer and the corresponding end of the tube and the fluid therein; and
operating the pump.

21. A method as defined in claim 20, wherein monitoring an output includes operating a readout in response to the output of the differential pressure transducer.

22. A method of testing a cement slurry, comprising:
flowing a sample of the cement slurry directly into a receptacle portion of a closed fluid circuit having valves through which the cement slurry is not to flow;
creating a pressure pulse within the closed fluid circuit on one side of the sample;
detecting whether the pressure pulse is transmitted across the sample; and
flowing the sample directly from the receptacle portion and out of the fluid circuit without passing through the valves.

23. A method of testing gelation of a gel forming treatment fluid, comprising:
impregnating a core sample with the gel forming treatment fluid;
applying a pressure pulse to one side of the impregnated core sample; and
detecting a pressure differential created across the impregnated core sample in response to the applied pressure pulse.

24. A method as defined in claim 23, further comprising squeezing the impregnated core sample.

25. A method as defined in claim 24, wherein squeezing the core sample includes:
retaining the core sample between a support member and a movable member movable relative to the support member; and
moving the movable member against the core sample towards the support member.

* * * * *